(12) United States Patent
Kupnik et al.

(10) Patent No.: US 8,276,433 B2
(45) Date of Patent: Oct. 2, 2012

(54) SENSOR FOR MEASURING PROPERTIES OF LIQUIDS AND GASES

(75) Inventors: Mario Kupnik, Mountain View, CA (US); Butrus T. Khuri-Yakub, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 380 days.

(21) Appl. No.: 12/800,635

(22) Filed: May 18, 2010

(65) Prior Publication Data
US 2011/0023582 A1   Feb. 3, 2011

Related U.S. Application Data

(60) Provisional application No. 61/216,565, filed on May 18, 2009.

(51) Int. Cl.
*G01N 7/00* (2006.01)
(52) U.S. Cl. ...................................... 73/31.02; 73/31.05
(58) Field of Classification Search ................ 73/31.02, 73/23.2, 31.01, 31.05
See application file for complete search history.

(56) References Cited

U.S. PATENT DOCUMENTS

| | | | | |
|---|---|---|---|---|
| 6,789,426 B2* | 9/2004 | Yaralioglu et al. | | 73/597 |
| 7,387,889 B2 | 6/2008 | Manalis | | |
| 8,000,835 B2* | 8/2011 | Friz et al. | | 700/230 |
| 8,076,821 B2* | 12/2011 | Degertekin | | 310/309 |
| 2005/0121734 A1* | 6/2005 | Degertekin et al. | | 257/414 |
| 2010/0180673 A1* | 7/2010 | Cable et al. | | 73/64.53 |

* cited by examiner

*Primary Examiner* — J M Saint Surin
(74) *Attorney, Agent, or Firm* — Lumen Patent Firm

(57) ABSTRACT

The present invention provides a device that measures at least one property of the liquid or gas, where the invention is a CMUT sensor that includes a substrate, a first layer disposed on the substrate, where the first layer includes a cavity, and a compound plate, where the compound plated includes a bottom plate, an intermediate plate and a top plate. According to the invention, the intermediate plate has at least one sample inlet, a sample cavity and at least one sample outlet, where the bottom plate is disposed on the first layer, and the cavity in the first layer is sealed by the compound plate. The cavity in the first layer can be a vacuum or contain a gas. The CMUT sensor can be disposed in an array of two or more sensors and connected electrically in parallel.

27 Claims, 7 Drawing Sheets

(c)

(d)

SENSOR FOR MEASURING PROPERTIES OF LIQUIDS AND GASES

CROSS-REFERENCE TO RELATED APPLICATIONS

This application claims priority from U.S. Provisional Patent Application 61/216,565 filed May 18, 2009, which is incorporated herein by reference.

STATEMENT REGARDING FEDERALLY SPONSORED RESEARCH OR DEVELOPMENT

This invention was made with government support under contract N66001-06-2030 awarded by DARPA. The U.S. government has certain rights in the invention.

FIELD OF THE INVENTION

The invention relates to liquid and gas sensors. More particularly, the invention relates to a top plate of a capacitive micromachined ultrasonic transducer (CMUT) having a hollow cavity for analyzing liquids and gases.

BACKGROUND

The problem exists of how to realize a powerful sensor that can determine various properties in liquids and gases, such as the presence of an analyte, the concentration of an analyte in a liquid or gas, the affinity and energetics of chemical bindings, and even the precise flow rate in microchannels. A further problem includes a means to weigh biomolecules, single cells and nanoparticles in fluids.

In any resonant system, such as a microresonator, the quality factor (Q) is of main interest. It is defined by the ratio of the vibrational energy stored in the system and the total energy lost per cycle. The higher Q, the better the frequency stability of the resonator, which translates to lower phase noise performance, the main parameter for lowest detection limits of mass-loading-based sensors. A microresonator for mass loading applications has to have contact to the gas or liquid of interest. This inevitably introduces a main damping source, and, thus, significantly compromises the quality factor. A good example of this dilemma is the design of nano-cantilevers for gas sensing applications. In order to maximize for high quality factors (up to 400), these nano-cantilevers were designed down to sizes of the mean free path at atmospheric pressure, which counteracts the main purpose of such sensor, i.e. to interact with the gas of interest in terms of mass loading to sense something. Another demonstrated solution, although impractical, is to operate the microresonator at reduced pressure to avoid the quality factor degrading viscous damping losses present at atmospheric pressure.

In general, a cantilever-based approach suffers from the fact that the moving object is completely surrounded by the medium, which results in higher damping due to higher viscous drag and acoustic pressure waves to more than one side.

For mass loading applications in gases, the approach of using CMUT-based instead of cantilever-based microresonators is successful, but in liquids even a CMUT-based microresonator is heavily damped due to the high acoustic energy loss into the liquid, mainly due to the higher density than compared to a gas. It has been shown that the achievable quality factors of CMUTs immersed in liquids is too low to be functional as mass-loading sensor. Theoretically the manipulation of the boundary condition inside a CMUT element, comprising several CMUT cells, from rigid baffle to pressure-released baffle should increase the quality factor Q significantly, but for this approach to work each cell must be surrounded by a non-active area, i.e. an area that behaves closely to a pressure-released baffle. Another approach considered was to actively actuate neighbouring cells with an out-of phase signal to increase the quality factor, but the improvement in terms of quality factor was marginal.

There are existing approaches for cantilever-based microresonators to overcome the problem of low Qs when immersed in liquids. Q-enhancement technique has been described that decreases the effective damping of the cantilever by using an external feedback amplifier and a phase shifter (in a feedback loop), which allows increasing the quality factor by more than one order of magnitude. The method allowed increasing the very low quality factor of a microfabricated cantilever from ~1 to ~31. However, simulations have shown that such Q-enhanced systems are highly non-linear and the external amplifier can start to dominate the system. Further, a quality factor of 31 is still low compared to values achieved in air (up to 400). The most promising approach for cantilever-based biosensors is to embed the microchannel inside the cantilever itself. The main idea is to confine the fluid of interest inside the resonant cantilever while leaving the cantilever itself in a gaseous environment, or vacuum.

What is needed is a device that measures at least one property of the liquid or gas, which can be related to the presence of a chemical species of interest, or to measure at least one property of one or several objects inside the liquid or gas.

SUMMARY OF THE INVENTION

The present invention provides a device that measures at least one property of the liquid or gas, where the invention is a CMUT sensor that includes a substrate, a first layer disposed on the substrate, where the first layer includes a cavity, and a compound plate, where the compound plate includes a bottom plate, an intermediate plate and a top plate. According to the invention, the intermediate plate has at least one sample inlet, a sample cavity and at least one sample outlet, where the bottom plate is disposed on the first layer and the cavity in the first layer is sealed by the compound plate.

In one aspect of the invention, the substrate can be doped silicon.

In another aspect of the invention, the first layer is an electrically insulating layer.

According to a further aspect, the cavity in the first layer includes a vacuum or a gas.

In one aspect of the invention the sample cavity includes a liquid or a gas.

In yet another aspect of the invention, the compound plate includes a compound plate perimeter, where the compound plate perimeter is entirely supported by the first layer, where the cavity in the first layer is disposed within the supported perimeter.

According to another aspect of the invention, a top surface of the compound plate is exposed to a vacuum or ambient surrounding, where the ambient surrounding can be air or gas.

In one aspect, the at least one sample inlet, the sample cavity or the at least one sample outlet are coated with a functionalization material that can include polymer, a protein, a porous material or an array of posts.

According to a further aspect of the invention, the CMUT sensor is actuated by a force such as an electrostatic force, an acoustic force, a transducer force, a piezoelectric force, a magnetoelectric force, or a mechanical force.

In another aspect of the invention, the first layer is an electrically insulating layer, where the bottom plate and the top plate are connected to electrical ground and the substrate is biased by a first DC voltage, where the first DC voltage is superimposed by a first AC signal.

According to one aspect of the invention, the first layer is an electrically insulating layer, where the bottom plate is connected to an electrical ground and the substrate is biased by a first DC voltage, where the first DC voltage is superimposed by a first AC signal, where the intermediate plate includes an electrically insulating material, where the top plate is biased with a second DC voltage. Here, the second DC voltage is superimposed with a second AC signal. Further, the first AC signal is independent from the second AC signal. Additionally, an array of the CMUT sensors are disposed in a pattern connected by the sample inlets and the sample outlets, where the first AC signal and the second AC signal are disposed to move a sample through the array or disposed to restrict the sample from moving through the array.

In another aspect of the invention, an array of the CMUT sensors are disposed in a pattern connected by the sample inlets and the sample outlets, where each substrate and each bottom plate are electrically grounded, where each intermediate plate includes an electrically insulating material, where each top plate is biased with a DC voltage and the DC signal is superimposed with an AC signal, where the pattern of CMUT sensors are sequentially actuated by the AC signal, where the sequentially actuated signals pump a sample along the CMUT pattern. Here, the pattern is disposed to provide functions that include switching, pumping and sensing.

According to another aspect of the invention, a lateral extension of the cavity in the first layer is larger than, equal to or smaller than a lateral extension of the sample cavity in the intermediate plate.

In a further aspect of the invention, the sample cavity includes an array of cavity elements connected to i) a top surface of the bottom plate, ii) a bottom surface of the top plate, or i) and ii).

According to another aspect of the invention, the first layer includes at least two cavities, and the compound plate includes at least two sample cavities connected by the sample outlets and the sample inlets, where the first layer and compound plate are disposed on a single substrate. Here, each sample cavity is actuated independently by an AC signal or a DC signal. Further the sample cavities are sequentially actuated to pump a sample through the sample cavities. Additionally, at least one sample cavity is actuated to restrict a sample in the sample cavity.

In one aspect, at least one sample well is connected to each sample input, where at least one CMUT and at least one sample well are disposed on a well plate.

According to another aspect, the sample inlets and the sample outlets are disposed to bring together at least two samples in the sample cavity.

In a further aspect of the invention, the CMUT sensor is integrated on a bio-chip, where the bio-chip includes other sensors or actuators disposed to form a lab on a chip system.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

For all mass loading applications in gases, the approach of using CMUT-based instead of e.g. cantilever-based microresonators is successful, but in liquids even a CMUT-based microresonator is heavily damped due to the high acoustic energy loss into the liquid, mainly due to the higher density of liquids compared to gases. Biology, however, tends to happen in aqueous solutions. For important biological and medical areas, such as lab on a chip and in a commercial use, the invention provides a new CMUT-based sensor technology that can be used in an advantageous way for gases and liquids, and outperforms existing approaches.

The invention provides a powerful sensor that can determine various properties in liquids and gases, such as the presence of an analyte, the concentration of an analyte in a liquid or gas, the affinity and energetics of chemical bindings, and even the precise flow rate in microchannels. Further, it can be used to weigh biomolecules, single cells and nanoparticles in fluids. The invention can measure at least one property of the liquid or gas, which can be related to the presence of a chemical species of interest, or to measure at least one property of one or several objects inside the liquid or gas.

According to the current invention, the CMUT-based microresonator has only one side of the moving object in contact with the sample of interest. The other side is terminated by the evacuated gap, which prevents any acoustic loss except the clamping losses. According to the invention, CMUT-based microresonators for mass loading applications achieve quality factors up to 400, but with a significantly larger active area.

In another aspect, a compound plate structure is supported on more than one location. In one embodiment, the compound plate is supported on a full 360° basis, which forms a completely enclosed cavity below the compound plate. This cavity can be completely evacuated, which eliminates acoustic losses through this cavity, or filled with gas according to a desired constituent and pressure.

Figure 1:
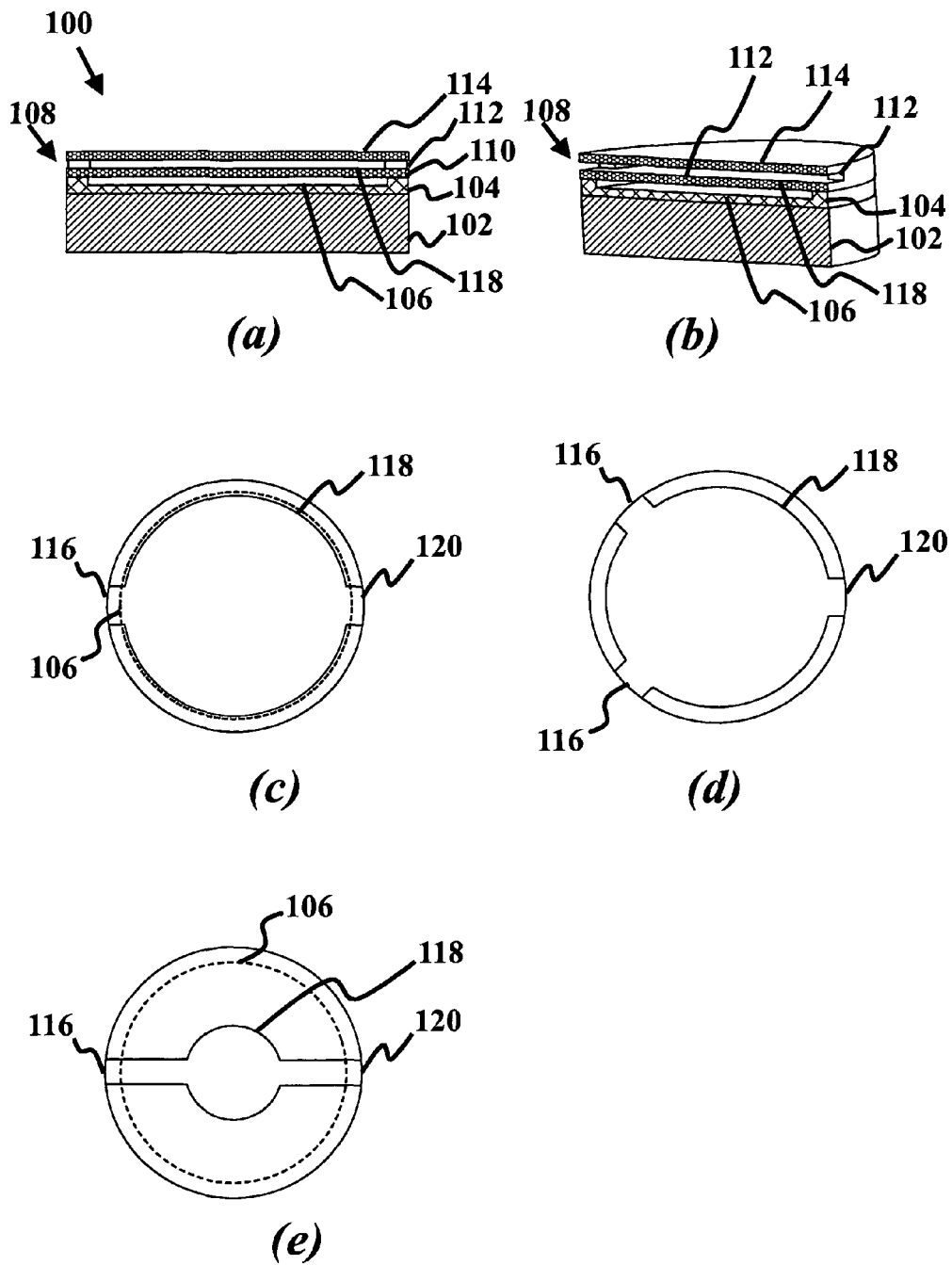
FIGS. 1a-1e show different configurations of the CMUT-based microresonator, according to the current invention.

Referring now to the figures, FIGS. 1a-1e show different configurations of the CMUT-based microresonator, according to the current invention. FIGS. 1a-1b show planar and perspective cutaway views or a CMUT sensor 100 that includes a substrate 102, a first layer 104 disposed on the substrate 102, where the first layer 104 includes a cavity 106, and a compound plate 108, where the compound plated 108 includes a bottom plate 110, an intermediate plate 112 and a top plate 114. According to the invention, the intermediate plate 112 has at least one sample inlet 116, a sample cavity 118 and at least one sample outlet 120, where the bottom plate 110 is disposed on the first layer 104, and the cavity 106 in the first layer 104 is sealed by the compound plate 108, where FIG. 1d shows two sample inlets 116. The geometric form of the intermediate plate 112 and sample cavity 118 can be of arbitrary shape or size, in which the liquid of interest will flow. Because the form of this sample cavity 118 can have any shape, this is more than the classical microfluidic channel.

As FIGS. 1c-1e show a top view of the CMUT sensor 100 with the top plate 114 removed for illustrative purposes and FIG. 1e further shows a reduced-size sample cavity 118 with the relatively larger diameter cavity 106 in the first layer 104 in dashed lines. As shown, at least one inlet channel 116 and one outlet channel 118 is required to allow a liquid to flow. The unit cell 100 in FIGS. 1a-1e is shown as circular cell 100, but any other shape such as hexagonal, rectangular, etc. can be utilized.

According to some aspects of the invention, at least two scenarios exist for the medium facing the top plate 114 of the compound plate 108. In one scenario, the cell 100 can be operated in vacuum, where it is totally encapsulated, or in another scenario, the cell 100 is exposed to air.

In one aspect, the CMUT sensor 100 has the compound plate that is actuated by a force such as an electrostatic force, an acoustic force, a transducer force, a piezoelectric force, a magnetoelectric force, or a mechanical force.

When viewing the sensors in FIGS. 1a-1e as harmonic oscillators with internal surface area A, with an effective mass m, and the resonance frequency f, the equation $$\frac{\Delta f}{f} = -\frac{1}{2}\left(\frac{A}{m}\right)\Delta\sigma.$$

in which Δf is the frequency shift due to the surface mass loading Δσ=Δm/A, is a first order approximation to explain the advantages of the current invention. Here, the smallest detectable surface mass loading is fully determined by the ratio of active surface area A to total mass m. Because the invention has a 360°-basis support of the compound plate 108 above the evacuated cavity 106, a lightweight structure with far larger active area A with even higher resonance frequency f is provided. This means the unit cell 100 always features a lightweight structure with larger area for a given resonance frequency f, where the sensor can be designed to be far more sensitive compared to other approaches, such as those that are only supported on one side.

The basic function of the sensor 100 can be explained as follows: A change in mass of the liquid due to the presence of one or several objects inside the liquid can be measured via monitoring the resonance frequency. This effect can be increased by functionalizing the channel walls, as shown in FIGS. 2a-2d, by coating a sample inlet 116, the sample cavity 118, the inside surface of the top plate 114 or a sample outlet 120 with a functionalization material 200, where the functionalization material 200 can include a polymer, a protein, a porous material, or an array of posts 202 that are coated with a functional layer to act as a sponge for specific chemicals or objects, or the sample cavity 118, the inside surface of the top plate 114 or a sample outlet 120 can include functional elements such as small posts 202 that are uncoated to increase the active surface area. Other choices for such a functionalization material are further proteins such as antibodies or enzymes, antigens, nucleic acids complementary to a nucleic acid under study, etc.

Another mode of operation is measuring the affinity and energetics of binding reactions in the liquid by monitoring the thermal induced frequency change or the thermal induced static capacitance change due to the change of static deflection of the compound plate. The sensor 100 even provides the platform to monitor such changes during chemical reactions (for example exothermic) between two arbitrary liquids that come in contact the first time right inside the compound plate. An example of such a cell design is given in FIG. 1d. By using at least two independent inlet channels 116, two liquids come into contact right at the location where both the sensing and the chemical reaction takes place over the same period of time. Further, the output of such a cell 100 in FIG. 1d can then be fed via the outlet channel 120 into another sensor cell or group of sensor cells, see for example FIG. 4a, where another measurement is made of this liquid output right after the chemical reaction is performed.

Figure 3:
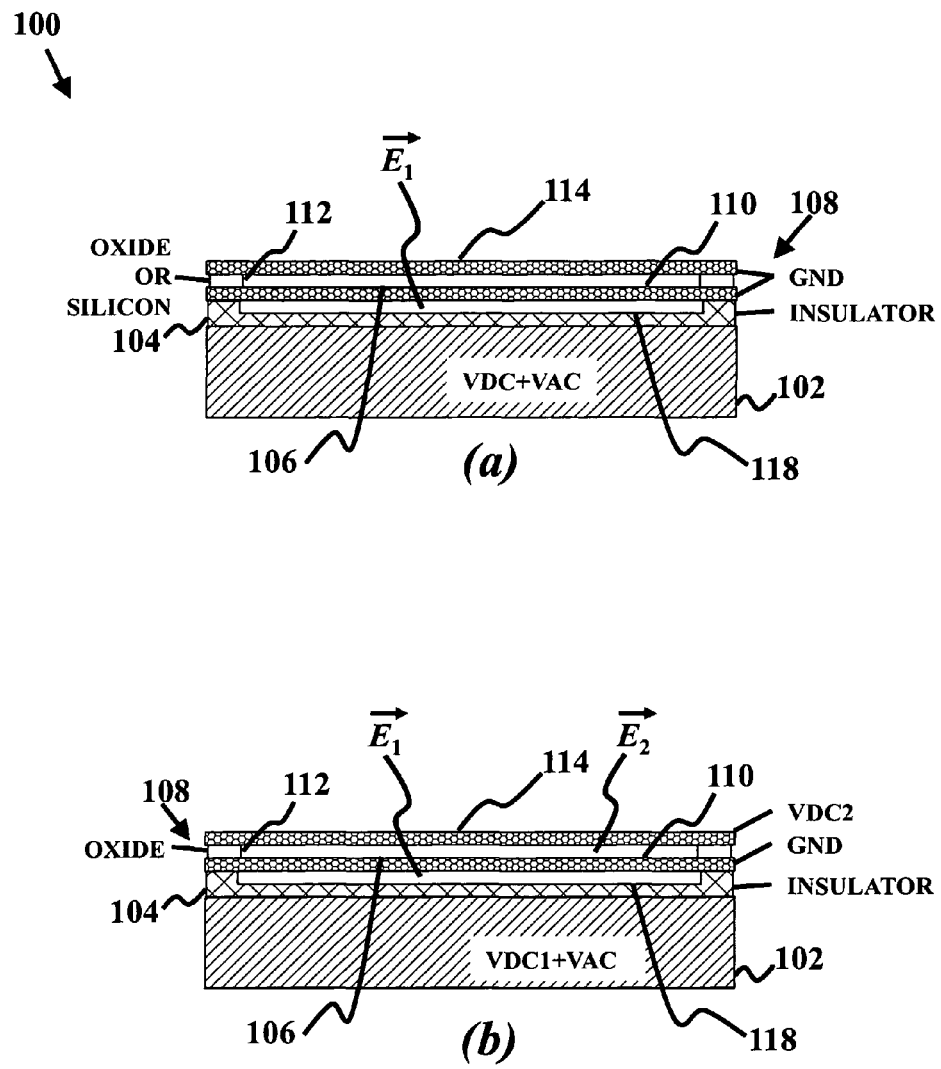
FIGS. 3a-3b show planar cutaway view of some biasing schemes for two examples of how to choose specific materials for the CMUT-based microresonator, according to the current invention.

An electrostatic force can easily be used to actuate the unit cell of the sensor. At least two electrical biasing schemes for two examples of how to choose specific materials are shown in the planar cutaway views of FIGS. 3a-3b. As shown in FIG. 3a, the compound plate 108 can be connected to electrical ground and the substrate 102 is biased by a DC voltage ($V_{DC}$), which is superimposed by an AC signal ($V_{AC}$). In this case the liquid is not penetrated by an electrical field, which is important for certain bio applications, in which for example living cells are investigated etc., rather the electric field $\vec{E}_1$ is in the cavity 118 in the first layer 104. Further, here the efficient mechanism of actuating this sensor by a large electric field $\vec{E}_1$ is beneficial, in the same way a CMUT is actuated, is beneficial. In these examples, the substrate 102 is doped silicon or any other electrically conductive material.

FIG. 3b shows a planar cross-section view of one cell 100, where the electric field $\vec{E}_1$ is in the cavity 118 in the first layer 104 and there is another electric field $\vec{E}_2$ penetrating the sample cavity 118, where the following scenarios may apply: the liquid sample in the sample cavity 118 can be non-conductive, either an additional top plate 114 or bottom plate 110 of the compound plate 108 is covered with an insulating material, or the entire sample cavity 118 is covered with an electrically conductive material. By using an electrical insulating material (e.g. silicon dioxide) for the intermediate plate 112 portion of the compound plate 108, the liquid can be intentionally penetrated by an electrical field $\vec{E}_2$ caused by a second electrical voltage ($V_{DC2}$), which might be advantageous for certain applications such as measuring the electrical capacitance/conductivity etc. of the liquid. In another example, the electric field $\vec{E}_2$ can be used to make sure that objects inside the liquid are attracted more to one side of the sample cavity 118 (top or bottom part) inside the compound plate 108, and such particles could be prevented from moving with the liquid flow by electrostatically fixating them in the sample cavity by turning on the electric field $\vec{E}_2$. Further, for electrically insulating liquids, the liquid channel can be seen as the dielectric material of a capacitor, i.e. the electrical capacitance provides additional information of the properties of the liquid, such as dielectric constant, or the electrical resistance of the liquid can also be monitored. Such information can be used for composition measurements etc. Further, the two electrical connections for the top plate 114 and bottom plate 110 of the compound plate 108 can be used to change the electrostatic force between these two parts of the compound plate 108. Basically, this will be done by another superimposed AC signal, which can be completely independent of $V_{AC}$, i.e. different frequency, phase, and amplitude. The effect of this additional electrostatic force is that the liquid will be squeezed, where this provides the mechanism for microfluidic pumping.

Another biasing scheme is to connect both the substrate 102 and the bottom plate 110 of the compound plate 108 to electrical ground and the top plate 114 to an optional DC signal superimposed by an AC signal. This provides another way to use the same structure of the cell 100 as pumping elements (microfluidic pump) between cells 100 used for sensing. Such a pumping cell 100, which can include several cells 100 lined up in one row, only requires the AC signal amplitude modulated in time and space along the cells 100 to pump the liquid along.

The cell 100 can also be disposed to realize a flow resistance device. By simply applying an electrical voltage between the top plate 114 and bottom plate 110 of the compound plate 108, the liquid flow rate can be reduced due to the electrostatic attraction of the bottom plate 110 and top plate 114 of the compound plate 108. In an example where an electrical insulation layer structure is embedded between to form the intermediate plate 112, the voltage can exceed the pull-in voltage of the top plate 114 and bottom plate 110 of the compound plate 108 to further reduce the open cross sectional area of the sample cavity 118.

According to a further aspect of the invention, the CMUT sensor 100 is actuated from the top plate 114 of the compound plate 108 and/or the bottom plate 110 of the compound plate 108.

In yet another aspect of the invention, the CMUT sensor 100 is actuated using signals in a range of DC to GHz.

Figure 2:
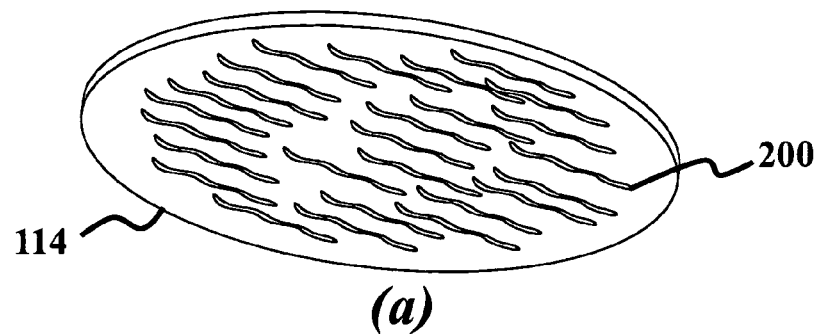
FIGS. 2a-2d show functionalizing of the sample channel walls and increasing the active surface area that can be functionalized, according to the current invention.
Figure 2:
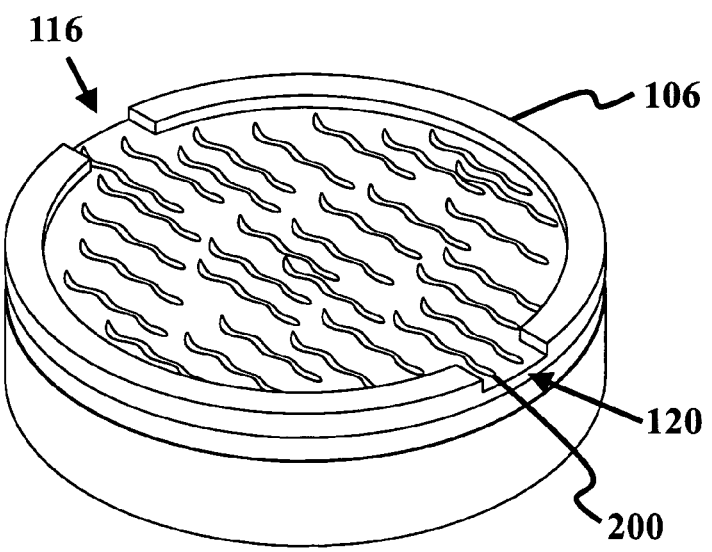
Figure 2:
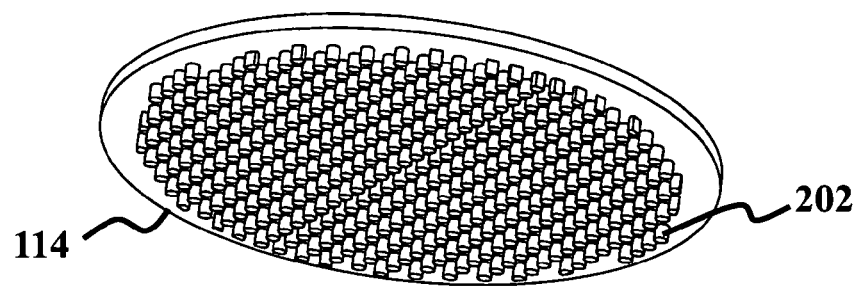
Figure 2:
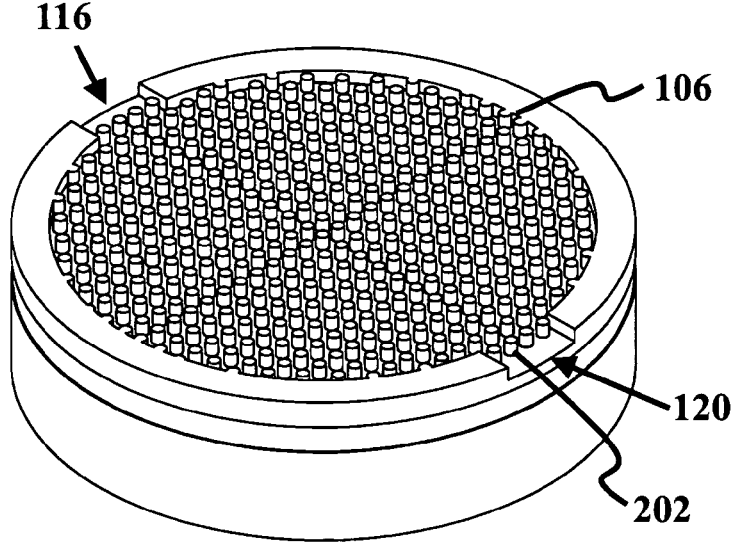

According to one aspect of the compound plate 108, the intermediate plate 112 structure determines the behaviour of the compound plate 108 in terms of the coupling mechanism, where FIGS. 2b-2c show how the posts 202 can mechanically couple the top plate 114 with the bottom plate 110 to form a increased active area in the sample cavity 118, which is advantageous when the height of the sample cavity 118 is required to be larger than the wavelength of the sound in the liquid sample, where the wavelength of the sound in the liquid sample depends on the excitation frequency of the compound plate 108 according to the resonant frequency of the compound plate 108. The height of the sample cavity 118 will be preferred to be in the sub wavelength range of the acoustic waves in the liquid. Further, as shown in FIGS. 1c and 1e, the radius of the cavity 106 in the first layer 104 for circular cells in relation to the lateral extension of the liquid-filled sample cavity 118, determines what dominates the coupling mechanism between the bottom and top part of the compound plate, which can be either acoustical or mechanical coupling or a combination of both, where the cavity 106 in the first layer 104 shown in FIGS. 1e and 1e is illustrated in dashed lines. In these scenarios, a configuration with similar lateral extension between the cavity 106 in the first layer 104 and sample cavity 118 will be mostly coupled by the liquid itself, that is by a pressure distribution inside the sample channel 118. This can be also seen as a boundary condition manipulation that is close to the pressure-released baffle condition, except that no active area is sacrificed as mentioned earlier, because when vacuum or gas is present at the top surface of the top plate 114 of the compound plate 108, then no significant acoustic loss can be generated away from the sensor 100, thus a high quality factor is preserved.

In a configuration in which the lateral extension of the sample channel 118 is smaller than the one from the cavity 106 in the first layer 104, as shown in FIG. 1e, the coupling will be a combination of both a mechanical coupling by the intermediate plate 112 of the compound plate 108 and by the liquid pressure distribution inside the sample cavity 118. The smaller radius sample cavity 118 (see FIG. 1e) in this case will reduce the active area of the sensor cell 100, which is unfavourable for certain applications, but can also be of advantage for situations where objects such as cells or biomolecules of a specific size are supposed to pass the sample cavity 118 one after the other to be sensed in a well controlled fashion.

Referring again to FIGS. 2c-2d, for applications where a large active area of the sample cavity 118 is advantageous, the more mechanically coupled compound plate 108 still can be realized. Shown in FIGS. 2c-2d, many small circular posts 200 are connecting the bottom plate 110 and top plate 114 of the compound plate 108, which provides a strong mechanical coupling and, even more important, an increased active area of the sensor cell 100, where the posts 200 can be triangular, hexagonal or any other shape. It is also possible to attach these small posts 200 only on one side of either the top plate 114 or bottom plate 110, where the active area is still increased but the coupling is then dominated by the liquid.

Figure 4:
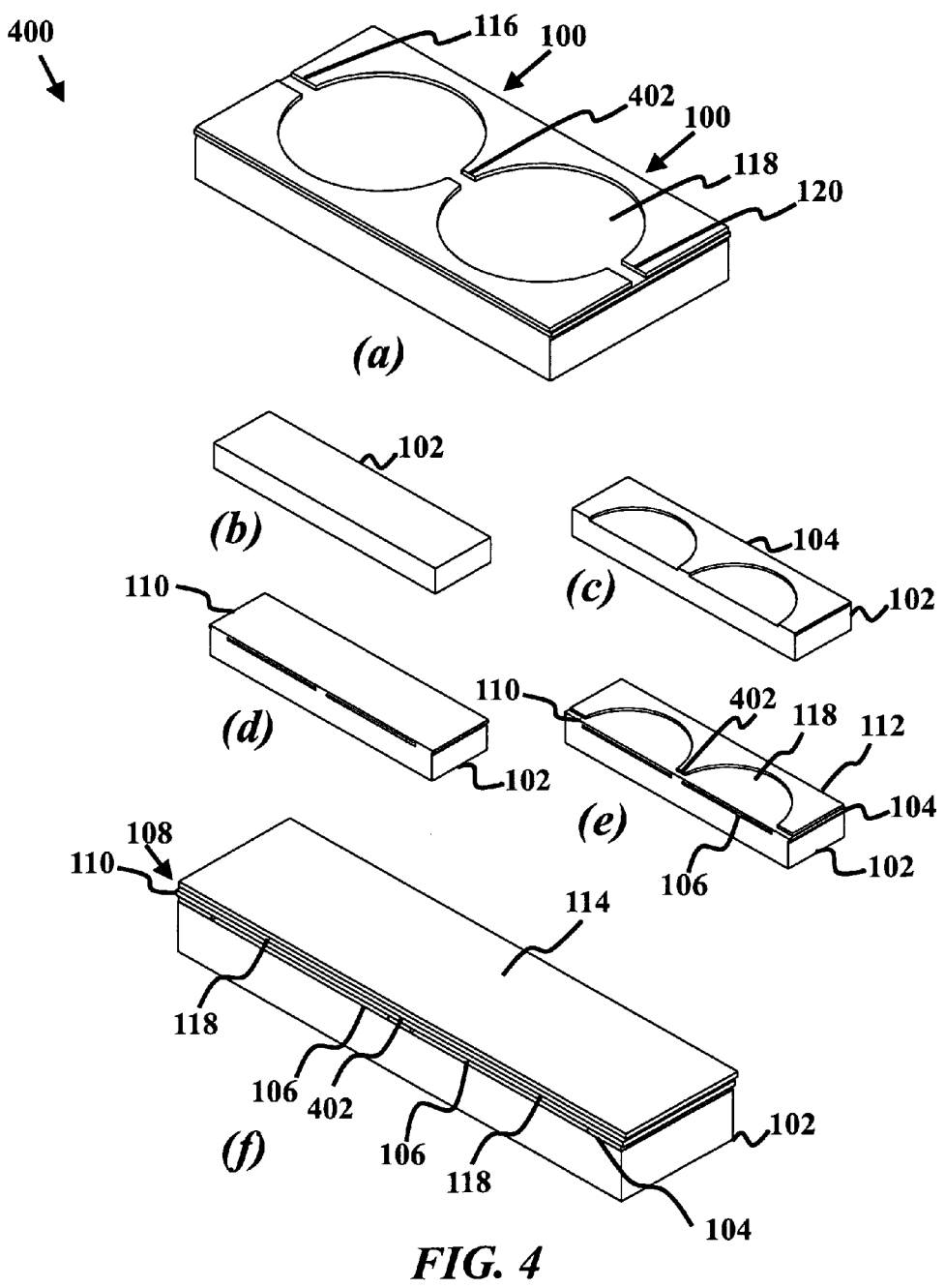
FIGS. 4a-4f show several cells disposed electrically in parallel and the steps for fabricating one or multiple cells, according to the current invention.

Because this cell 100 of the current invention is CMUT-based, it also benefits from the advantage associated with parallelism. By combining several of these cells 100 electrically in a parallel element configuration 400 as shown in FIG. 4a, the active area is increased and the frequency monitoring is simplified, where the top plate 114 is removed for illustrative purposes. Multiple parallel cells 400 provide a significantly-reduced motional impedance and a large sensing signal, resulting in a better signal to noise ratio, where two cells 100 are shown for illustrative purposes but it is understood that any number of cells 110 can be provided. This enables the sensor of the current invention to be used directly as a microresonator in an oscillator circuit.

In addition to the inlet channel 116 and outlet channel 120 for the liquid, the element includes a connection channel 402 disposed to connect adjacent sample cavities 118. The two cavities 106 in the first layers 104, which may be evacuated cavities 106, below the compound plate 108 do not need to be connected, although this is possible. The parallel element configuration 400 as shown in FIG. 4a can be extended to any desired number of cells 100 in both lateral extensions x and y, and several elements 400 can be combined to form a complete sensor array, in which for example each element 400 is functionalized with a different material (e.g. polymer) for orthogonal sensing.

Another way of operating the parallel element configuration 400, as shown in FIG. 4a, is given as follows. Assuming the two cells 100 can be addressed individually in terms of their electrical connections on the substrate 102, the element 100 can be used to determine the flow velocity of the liquid with very high precision. Assume the sample cavity 118 is filled with gas first and then the liquid starts to flow into the inlet channel 116 of the element 100. First, the resonant frequency of the cell 100 on the left hand side in the parallel element configuration 400 as shown in FIG. 4a will drop, then the second cell on the right hand side will show the same resonance frequency drop over time. Because the pitch between the two cells 100 is known with high precision (micromachined), the two frequency-over-time curves can be correlated to each other, which provides the information of delay with high precision and, therefore, the flow velocity can be calculated with high precision by simply dividing the pitch by this delay. The liquid flow itself can be interrupted, for example by adding bubbles, such as air bubbles, into the liquid by intention, so that liquid flow follows air flow, or that at least one object with increased density compared to the liquid is introduced into the inlet channel 116, where an increase or decrease in density compared to the flowing liquid or gas sample is provided. Examples for the introduced object case are nanoparticles, singles cells, or all kinds of bio molecules. The two-cell element 400 allows determining the flow speed with high precision, and it can also be used for counting such single objects in the liquid, for example counting of cells or nanoparticles.

In another aspect of the invention, as shown in FIGS. 4a-4f, an array 400 of the CMUT sensors 100 are disposed in a pattern connected by the sample inlets 116 and the sample outlets 120, where each substrate 102 and each bottom plate 110 are electrically grounded, where each intermediate plate 112 includes an electrically insulating material, where each top plate 114 is biased with a DC voltage and the DC signal is superimposed with an AC signal (see FIG. 3b), where the pattern of CMUT sensors are sequentially actuated by the AC signal, and where the sequentially actuated signals pump a sample along the CMUT pattern 400. This configuration requires an electrical insulator disposed between the top plate 114 and the bottom plate 110, such as an electrically insulating intermediate plate 112, or by using electrically insulating plate materials in the compound plate 108 with patterned metal electrodes in the top plate 114 and bottom plate 110, or by etching insulation trenches into the substrate 102 from the back side. FIGS. 4a-4f show the pattern can be disposed to provide functions that include switching, pumping and sensing. Here, each sample cavity 118 can be actuated independently by an AC signal or a DC signal. Further the sample cavities 118 are sequentially actuated to pump a sample through the sample cavities 118. Additionally, at least one sample cavity 118 can be actuated to restrict a sample in the sample cavity 118.

The sensor can be fabricated with different microfabrication techniques. One example of such a fabrication process flow of how to realize the sensor is shown in FIGS. 4b-4f. It is based on a combination of surface and bulk micromachining techniques.

The main steps are described as following:

FIG. 4b shows a doped substrate 102 (e.g. silicon) with flat and smooth surface as the starting point of the fabrication.

FIG. 4c shows the substrate 102 is oxidized to form a uniform first layer 104 of oxide, and this oxide is patterned to form the cavities 106 for the electrostatic actuation below the compound plate 108 (see FIG. 4C. The insulation first layer 104 can be extended into the substrate to increase the reliability in terms of electrical breakdown and to reduce the parasitic capacitance of the device.

FIG. 4d shows the next step, after the electrical insulation first layer 104 structure is formed on the substrate 102, the bottom plate 110 of the compound plate 108 is transferred to the assembly. According to the invention, one way of doing this is by transferring the active layer of a silicon-on-insulation (SOI) wafer via wafer bonding. Because the bonding step can be performed in a vacuum chamber, the gap will be evacuated.

FIG. 4e shows the next step, which includes fabricating the intermediate layer 112 of the compound plate 108. There are many ways to do this. For example, one can oxidize the assembly and then pattern this oxide to get a structure as shown in FIG. 4e, which includes a sample cavity 110, an input channel, an output channel, 102, and in the case of parallel element configuration 400 a connection channel 402.

Another method would be to remove only the handle wafer of the SOI wafer, i.e. to use the buried oxide layer (BOX) as intermediate plate 112 of the compound plate 108. In this case, instead of stripping the box layer completely, it is patterned by standard lithography and liquid or plasma etching techniques. Another way is just to etch into the silicon, i.e. into the bottom plate 110 of the compound plate 108 with liquid or plasma etching. Another way to do this is to bond the substrate 102 to another SOI wafer that was oxidized and subsequently patterned. In the latter case alignment bonding capability is required, which can be done with high precision (down to 200 nm). Another way to fabricate the compound plate 108 is by oxidizing the substrate 102 in FIG. 4d and then patterning the oxide with standard lithography and liquid (buffered oxide etch) or plasma etching. Note that in this step the inlet channel 116 and outlet channel 120, as well as the connection channel 402 between the cells 100 are realized. Further, this step would also be the step in which posts 402, as shown in FIG. 2b, would be realized.

The last step is to transfer another active layer to the wafer via wafer bonding, as shown in FIG. 4f, and then the handle wafer and BOX layer of this SOI waver are removed before electrical contacts to the substrate and the compound plate, or parts of it (as discussed in FIGS. 3a-3b), are realized. Because the sample cavity 118 is open to ambient, no vacuum is required during the bonding step here, although it might be advantageous to use a bonder with vacuum capability for this step as well.

The sensor is then ready to be connected to a liquid channel via standard flanges. Poly Dimethyl Siloxane (PDMS) or other standard materials can be used for this purpose.

Another important aspect of this invention is the following: Although this invention describes having liquid inside the compound plate, the sensor can also be used for gases with the potential of significant improvements compared to other state-of-the-art sensors. Some advantages are that the gas volume that each cell 100 is exposed to is better controlled, where the cell 100 can be fed from a concentrator to further increase the level of detection, and that the time constants are improved significantly compared to other CMUT-based gas sensors, in which the volume of the sample cavity 118 being filled with gas in front of the sensor 400 is several orders of magnitude smaller, where it is desirable to confine the sample species to a small volume that is disposed close to the sensing cell 100. than to this micromachined equivalent. Therefore, the scope of the invention is focussed on liquid sensing applications but not limited to, i.e. also gas-sensing applications are considered.

This sensor technology opens the door to applications wherever the biomolecular detection in liquid solutions is required. Examples are pharmaceutical (clinical diagnostic testing laboratories) and biological research (e.g. cell counting) and fabrication, life sciences, medical diagnostics such as blood and urine analysis, monitoring for drug delivery, homeland security applications, warfare detection, environmental and food quality monitoring.

Further, the sensor technology can be used for accurate mass flow measurements, for example as a mass flow controller in the micro to nano-liter range and for manipulating liquid flows (change of flow resistance and pumping inside microchannels).

Figure 5:
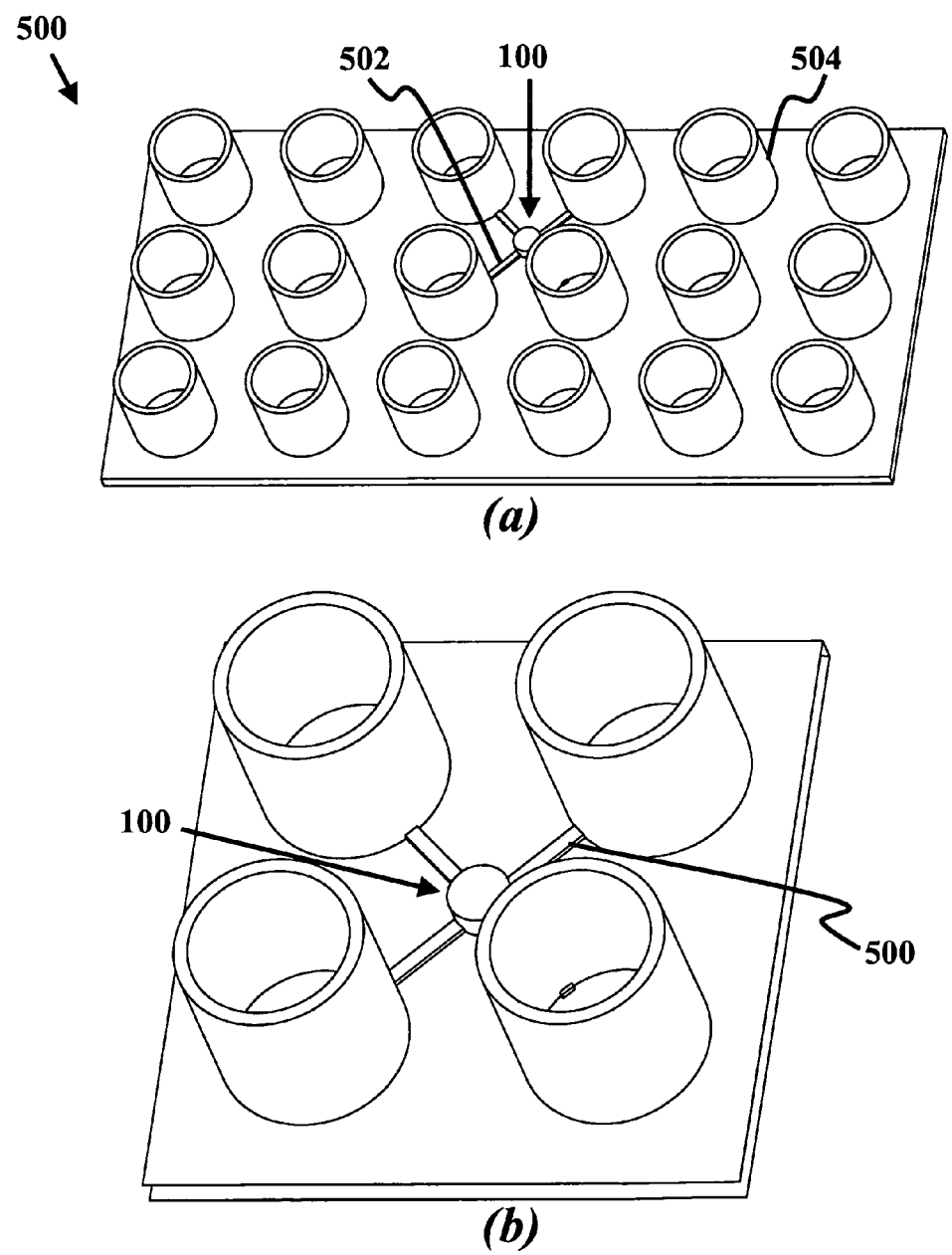
FIGS. 5a-5b show a 2:3 well plate with embedded microchannels and sensor, according to the current invention.

Another application is to use this sensor technology for lab-on-a-chip applications and for smart well plates. The latter example is illustrated in FIGS. 5a-5b, where a 2:3 well plate 500 with embedded microchannels 502 and sensor 100 is shown, where the microchannels 502 connect the sensor 100 to the wells 504. Only one sensor is shown in FIGS.

5a-5b, but there can be one or more sensors per well, which will allow efficient clinical diagnostic testing.

The current invention can be operated totally in vacuum for highest quality factors. However, this requires a complete sensor vacuum encapsulation associated with challenges in terms of hermetic sealing requirements. Because the sensor according to the current invention features on one side of the compound plate an evacuated gap high quality factors are attained (measured values up to ~400) even if the sensor is not vacuum encapsulated on the packaging level. This is an advantage over other sensors because of their higher acoustic loss (both sides) and far higher viscous drag, even in air. Note that in all of these considerations the resonance frequency f is the key parameter.

Another advantage of the sensor technology in the current invention is that it is based on CMUT technology, i.e. it inherently provides a well matched parallel structure in terms of lateral and vertical dimensions, and, this, in terms of matching of resonance frequencies of many cells operating in parallel. The main reason for this is that the moving part of a CMUT-like structure is not etched itself. In summary, in a CMUT element the frequency variation between the cells 100 depends less on the lithography and etching. The sensor technology of the current invention can be expected to be far more reliable in terms of mechanical robustness and issues during fabrication.

Because the sensor technology of the current invention allows a realization that goes more in a two dimension, i.e. circular, it allows fabrication of more complex channel structures, such as several channels in one compound plate 108 etc.

The current invention does not require laser and position sensitive detector (PSD). Because of the high efficiency of the CMUT-based sensor technology and the already mentioned advantage of easier realization of a well-matched parallel structure comprising many uniform cells, the current invention can directly be operated in an oscillator circuit as microresonator. This is essential for monolithic integration of the sensor with an ASIC and will help to establish this sensor technology for various commercial products because of lower price and smaller space requirements.

The current invention offers more flexibility, where more than one inlet channel 116 and outlet channel 120 per cell 100 is possible (see FIG. 1d, and FIG. 5b), which allows mixing two liquids right at the location where both the sensing and the chemical reaction takes place over the same period of time.

Similar to the CMUT technology itself, integration with electronics, also monolithically, is possible according to the invention.

The sensor according to the invention can be used to manipulate the liquid or objects (e.g. nanoparticles or cell) inside the liquid. As discussed, variations for microfluidic pumping and changing the flow resistance inside a microfluidic channel, and the invention is perfectly compatible with well plates 500 for analytical research and clinical diagnostic testing.

Figure 6:
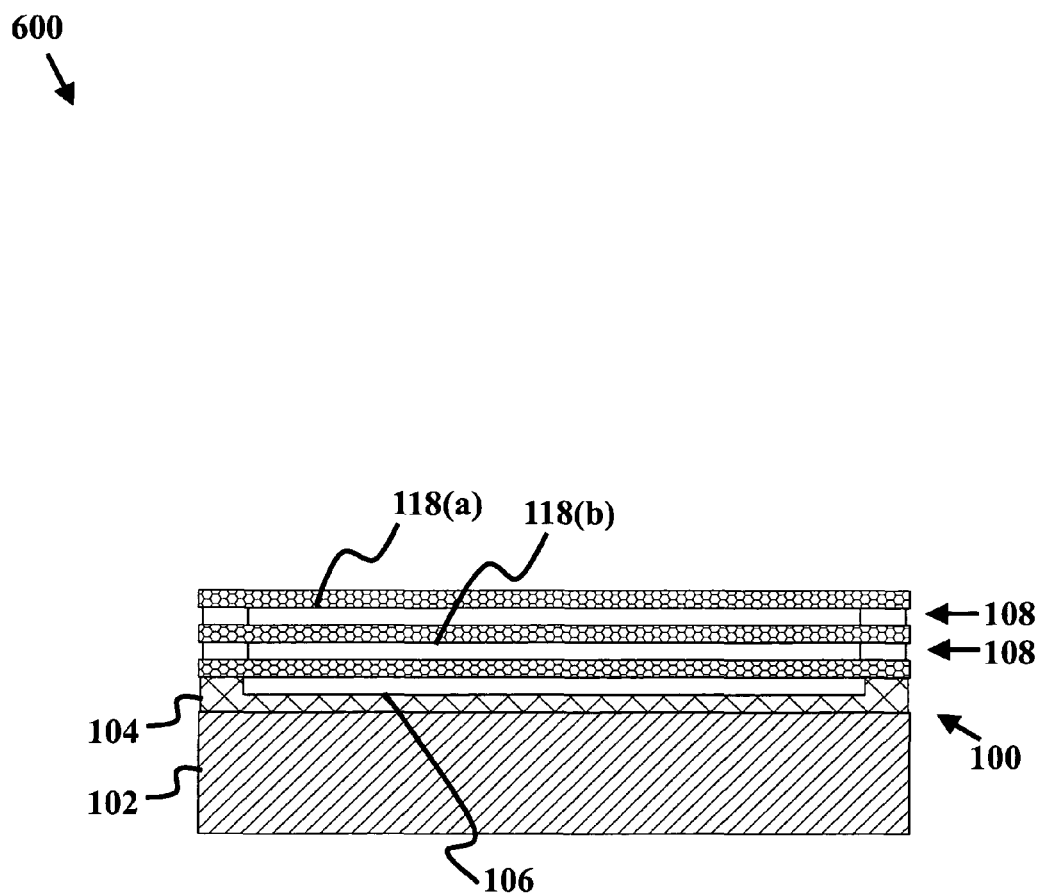
FIG. 6 shows a stacked configuration of the unit cell having a stack of compound plates, according to the current invention.

FIG. 6 shows a stacked configuration 600 of the unit cell 100 having a stack of compound plates 108, where also shown is the substrate 102, and the cavity 106 in the first layer 104, where two compound layers 108 are shown for illustrative purposes and it is understood that many compound layers 108 can be stacked. FIG. 6 further shows a top sample cavity 118 (a) and a bottom sample cavity 118 (b), where the stacked sensor 600 can be operated in several scenarios. In one aspect the top plate 114 is exposed to vacuum or gas with the first sample chamber 118 (a) and second sample chamber 118 (b) containing liquid samples. In another aspect the top plate 114 is exposed to vacuum or gas with the first sample chamber 118 (a) and second sample chamber 118 (b) containing gas samples. In a further aspect the top plate 114 is exposed to vacuum or gas with the first sample chamber 118 (a) containing a gas sample and second sample chamber 118 (b) a containing liquid sample. In another aspect the top plate 114 is exposed to vacuum or gas with the first sample chamber 118 (a) containing a liquid sample and second sample chamber 118 (b) a containing gas sample.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A CMUT sensor comprising:
   a. a substrate;
   b. a first layer disposed on said substrate, wherein said first layer comprises a cavity; and
   c. a compound plate, wherein said compound plate comprises a bottom plate, an intermediate plate and a top plate, wherein said intermediate plate comprises at least one sample inlet, a sample cavity and at least one sample outlet, wherein said bottom plate is disposed on said first layer, wherein said cavity in said first layer is sealed by said compound plate.

2. The CMUT sensor of claim 1, wherein said substrate comprises doped silicon.

3. The CMUT sensor of claim 1, wherein said first layer is an electrically insulating layer.

4. The CMUT sensor of claim 1, wherein said cavity in said first layer includes a vacuum or a gas.

5. The CMUT sensor of claim 1, wherein said sample cavity includes a liquid or a gas.

6. The CMUT sensor of claim 1, wherein said compound plate comprises a compound plate perimeter, wherein said compound plate perimeter is entirely supported by said first layer, wherein said cavity in said first layer is disposed within said supported perimeter.

7. The CMUT sensor of claim 1, wherein a top surface of said compound plate is exposed to a vacuum or ambient surrounding, wherein said ambient surrounding is selected from the group consisting of air and gas.

8. The CMUT sensor of claim 1, wherein said at least one sample inlet, said sample cavity or said at least one sample outlet are coated with a functionalization material selected from the group consisting of a polymer, a protein, a porous material, and an array of polymer posts.

9. The CMUT sensor of claim 1, wherein said compound plate is actuated by a force selected from the group consisting of electrostatic force, acoustic force, transducer force, piezoelectric force, magnetoelectric force, and mechanical force.

10. The CMUT sensor of claim 1, wherein said first layer is an electrically insulating layer, wherein said bottom plate and said top plate are connected to electrical ground and said substrate is biased by a first DC voltage, wherein said first DC voltage is superimposed by a first AC signal.

11. The CMUT sensor of claim 1, wherein said first layer is an electrically insulating layer, wherein said bottom plate is connected to an electrical ground and said substrate is biased by a first DC voltage, wherein said first DC voltage is superimposed by a first AC signal, wherein said intermediate plate comprises an electrically insulating material, wherein said top plate is biased with a second DC voltage.

12. The CMUT sensor of claim 11, wherein said second DC voltage is superimposed with a second AC signal.

13. The CMUT sensor of claim 12, wherein said first AC signal is independent from said second AC signal.

14. The CMUT sensor of claim 12, wherein an array of said CMUT sensors are disposed in a pattern connected by said sample inlets and said sample outlets, wherein said first AC signal and said second AC signal are disposed to move a sample through said array or disposed to restrict said sample from moving through said array.

15. The CMUT sensor of claim 1, wherein an array of said CMUT sensors are disposed in a pattern connected by said sample inlets and said sample outlets, wherein each said substrate and each said bottom plate are electrically grounded, wherein each said intermediate plate comprises an electrically insulating material, wherein each said top plate is biased with a DC voltage and said DC signal is superimposed with an AC signal, wherein said pattern of CMUT sensors are sequentially actuated by said AC signal, wherein said sequentially actuated signals pump a sample along said CMUT pattern.

16. The CMUT sensor of claim 15, wherein said pattern is disposed to provide functions selected from the group consisting of switching, pumping and sensing.

17. The CMUT sensor of claim 1, wherein a lateral extension of said cavity in said first layer is larger than, equal to or smaller than a lateral extension of said sample cavity in said intermediate plate.

18. The CMUT sensor of claim 1, wherein said sample cavity comprises an array of cavity elements connected to i) a top surface of said bottom plate, ii) a bottom surface of said top plate, or i) and ii).

19. The CMUT sensor of claim 1, wherein said first layer comprises at least two said cavities and said compound plate comprises at least two said sample cavities connected by said sample outlets and said sample inlets, wherein said first layer and said compound plate are disposed on a single said substrate.

20. The CMUT sensor of claim 19, wherein each said sample cavity is actuated independently by an AC signal or a DC signal.

21. The CMUT sensor of claim 20, wherein said sample cavities are sequentially actuated to pump a sample through said sample cavities.

22. The CMUT sensor of claim 20, wherein at least one said sample cavity is actuated to restrict a sample in said sample cavity.

23. The CMUT sensor of claim 1, wherein at least one sample well is connected to each said at least one sample input, wherein at least one said CMUT and said at least one sample well are disposed on a well plate.

24. The CMUT sensor of claim 1, wherein said sample inlets and said sample outlets are disposed to bring together at least two samples in said sample cavity.

25. The CMUT sensor of claim 1, wherein said CMUT sensor is actuated from i) said top plate of said compound plate, ii) said bottom plate of said compound plate or i) and ii).

26. The CMUT sensor of claim 1, wherein said CMUT sensor is actuated using signals in a range of DC to GHz.

27. The CMUT sensor of claim 1, wherein said CMUT sensor is integrated on a bio-chip, wherein said bio-chip comprises other sensors or actuators disposed to form a lab on a chip system.

* * * * *